(12) United States Patent
Fischer, Jr.

(10) Patent No.: US 9,855,401 B2
(45) Date of Patent: Jan. 2, 2018

(54) MULTI-LUMEN BIOLOGIC-DELIVERING DEVICE

(71) Applicant: Muffin Incorporated, West Lafayette, IN (US)

(72) Inventor: Frank J. Fischer, Jr., Bloomington, IN (US)

(73) Assignee: MUFFIN INCORPORATED, West Lafayette, IN (US)

( * ) Notice: Subject to any disclaimer, the term of this patent is extended or adjusted under 35 U.S.C. 154(b) by 0 days.

(21) Appl. No.: 15/159,025

(22) Filed: May 19, 2016

(65) Prior Publication Data

US 2016/0263347 A1 Sep. 15, 2016

Related U.S. Application Data

(62) Division of application No. 13/943,314, filed on Jul. 16, 2013, now Pat. No. 9,393,364.

(60) Provisional application No. 61/672,496, filed on Jul. 17, 2012.

(51) Int. Cl.
*A61M 31/00* (2006.01)
*A61M 5/32* (2006.01)
(Continued)

(52) U.S. Cl.
CPC .......... *A61M 25/007* (2013.01); *A61M 5/158* (2013.01); *A61M 5/329* (2013.01);
(Continued)

(58) Field of Classification Search
CPC .... A61M 5/158; A61M 5/3286; A61M 5/329; A61M 5/3291; A61M 5/3295; A61M 5/3298; A61M 3/00; A61M 5/00; A61M 5/14; A61M 5/1407; A61M 5/32; A61M 5/3297
(Continued)

(56) References Cited

U.S. PATENT DOCUMENTS 4,403,983 A 9/1983 Edelman et al.
4,675,004 A 6/1987 Hadford et al.
(Continued)

FOREIGN PATENT DOCUMENTS

CN 101239218 A 8/2008
WO WO 01/37916 A1 5/2001
(Continued)

OTHER PUBLICATIONS

Espacenet English Translation of CN 101239218.
International Search Report and Written Opinion for related PCT/US2013/050782, dated Sep. 25, 2013.

*Primary Examiner* — Jason Flick
(74) *Attorney, Agent, or Firm* — Woodard, Emhardt, Moriarty, McNett & Henry, LLP

(57) ABSTRACT

Arrangements and methods for delivering bioactive agents and/or cells into an extended volume of tissue are disclosed. In one embodiment, a cell-delivering needle arrangement has a tube positioned within a tube and fixedly attached to a wall thereof. In one exemplary method, a cell-delivering needle is advanced into tissue, a suspension of cells is passed through a first lumen and out of side ports, and a suspension of cells is passed through a second lumen and out of a distal opening. Other embodiments are disclosed.

21 Claims, 13 Drawing Sheets

(51) Int. Cl.
*A61M 25/00* (2006.01)
*A61M 5/158* (2006.01)

(52) U.S. Cl.
CPC ........ *A61M 5/3286* (2013.01); *A61M 5/3291* (2013.01); *A61M 5/3295* (2013.01); *A61M 5/3298* (2013.01); *A61M 2202/0064* (2013.01); *A61M 2202/097* (2013.01)

(58) Field of Classification Search
USPC .......................................................... 604/506
See application file for complete search history.

(56) References Cited

U.S. PATENT DOCUMENTS

| | | |
|---|---|---|
| 4,682,978 A | 7/1987 | Martin |
| 5,380,276 A * | 1/1995 | Miller ................... A61M 1/285 |
| | | 604/264 |
| 5,858,009 A | 1/1999 | Jonkman |
| 6,120,520 A | 9/2000 | Saadat et al. |
| 6,464,662 B1 | 10/2002 | Raghavan et al. |
| 6,520,936 B1 | 2/2003 | Mann |
| 6,572,579 B1 | 6/2003 | Raghavan et al. |
| 2002/0177822 A1 | 11/2002 | St. Cyr et al. |
| 2004/0215130 A1 | 10/2004 | Rioux et al. |
| 2008/0294096 A1 * | 11/2008 | Uber, III ................ A61M 5/142 |
| | | 604/66 |
| 2010/0063460 A1 | 3/2010 | Reed et al. |
| 2010/0076397 A1 | 3/2010 | Reed et al. |
| 2010/0331814 A1 | 12/2010 | Bates |
| 2011/0014181 A1 * | 1/2011 | Thornton ............... A61K 45/06 |
| | | 424/130.1 |

FOREIGN PATENT DOCUMENTS

| | | |
|---|---|---|
| WO | WO 2011/094379 A1 | 8/2011 |
| WO | WO 2012/059456 A1 | 5/2012 |
| WO | WO 2012/151751 A1 | 11/2012 |

* cited by examiner

MULTI-LUMEN BIOLOGIC-DELIVERING DEVICE

CROSS-REFERENCE TO RELATED APPLICATIONS

This application is a divisional of U.S. application Ser. No. 13/943,314, filed Jul. 16, 2013, which claims the benefit of U.S. Provisional Application No. 61/672,496, filed Jul. 17, 2012, both of which are hereby incorporated by reference in their entirety.

FIELD

The present invention relates generally to biologic-delivering needles and cannulas.

BACKGROUND

Critical limb ischemia (also referred to as "CLI") is a severe obstruction of the arteries in the extremities of the body, often the lower extremities including the leg, that results in a significantly reduced blood-flow. CLI can result in severe pain, skin ulcers or sores and, if left untreated, may result in amputation of the affected limb. CLI is unlikely to improve on its own and therefore often requires intervention from a medical professional.

Various bioactive agents and biologic materials such as cells, including stem cells, are currently being researched and used to treat CLI. In some of these treatments, a series of injections are made along the length of the patient's limb. Due to limited perfusion of the bioactive agent and/or biologic material, a large number of injections are often required to sufficiently spread the bioactive agent and/or biologic material throughout the tissue of the limb.

There exists a need for needle arrangements and associated methods that can deliver bioactive agents and/or biologic materials into an extended volume of tissue in a patient. Similarly, there exists a need for needle arrangements and associated methods that can sufficiently perfuse bioactive agents and/or biologic materials into tissue.

SUMMARY

In certain aspects, the present disclosure provides devices and methods for the delivery of biologic materials and/or bioactive agents into an extended volume of tissue. In accordance with some forms of the disclosure, such devices and methods are arranged to deliver a suspension of biologic material from a first lumen and a second lumen. In one embodiment, a method of delivering biologic material into an extended volume of tissue of a patient comprises: advancing a distal end region of a biologic-material-delivering needle having an elongated body defining a first lumen, a second lumen, a plurality of side ports associated with the first lumen, an end port associated with the second lumen, and a tissue-penetrating tip through the skin of the patient; passing a first suspension of biologic material through the first lumen and out of the side ports associated with the first lumen to release a biologic material from the side ports towards tissue adjacent to the elongated body; and passing a second suspension of biologic material through the second lumen and out of the end port associated with the second lumen to release a biologic material from the end port into tissue of the patient. In some instances, the second lumen is defined by a second elongate body positioned within the first lumen and fixedly coupled to a wall thereof. Additionally, in some aspects, the plurality of side ports are positioned around the periphery of the elongated body. The method may also comprise withdrawing the biologic-material-delivering needle while passing a suspension of biologic material into the biologic-material-delivering needle tract. In some instances, the biologic material comprises a plurality of cells.

In one embodiment, the present disclosure teaches a needle comprising a needle body having a proximal end region, a distal end region, and a sidewall; the needle body defining a first lumen extending from the proximal end region to the distal end region; the first lumen terminating in a closed distal end and communicating with a plurality of ports defined by the sidewall; the needle body defining a second lumen extending from the proximal end region to the distal end region and communicating with a distal opening in the distal end region; and the distal end region having a tissue-penetrating tip. In some instances, the first lumen and a second lumen are fixedly positioned to one another. Additionally, in some aspects, the plurality of side ports are positioned around the periphery of the elongated body. In some embodiments, the second lumen is positioned within the first lumen.

In one aspect, the present disclosure provides a fluid delivering needle comprising a needle body having a proximal end region, a distal end region, a first elongated body, and a second elongated body; the first elongated body having a sidewall defining a first lumen extending from the proximal end region to the distal end region; the first lumen terminating in a closed distal end and communicating with a plurality of ports defined by the sidewall and positioned around the periphery of the first elongated body; the second elongated body positioned within the first lumen and fixedly coupled to a wall thereof; the second elongated body defining a second lumen extending from the proximal end region to the distal end region and communicating with a distal opening in the distal end region; and the distal end region of the needle body having a tissue-penetrating needle tip. In some instances, the side ports have a cross-sectional area that is smaller than a cross-sectional area of the distal opening. Additionally, in some aspects, the second lumen has a cross-sectional area that is smaller than a cross-sectional area of the first lumen. In some embodiments, the needle further comprises a plug closing the distal end of the first lumen.

DESCRIPTION OF THE ILLUSTRATED EMBODIMENTS

Figure 1:
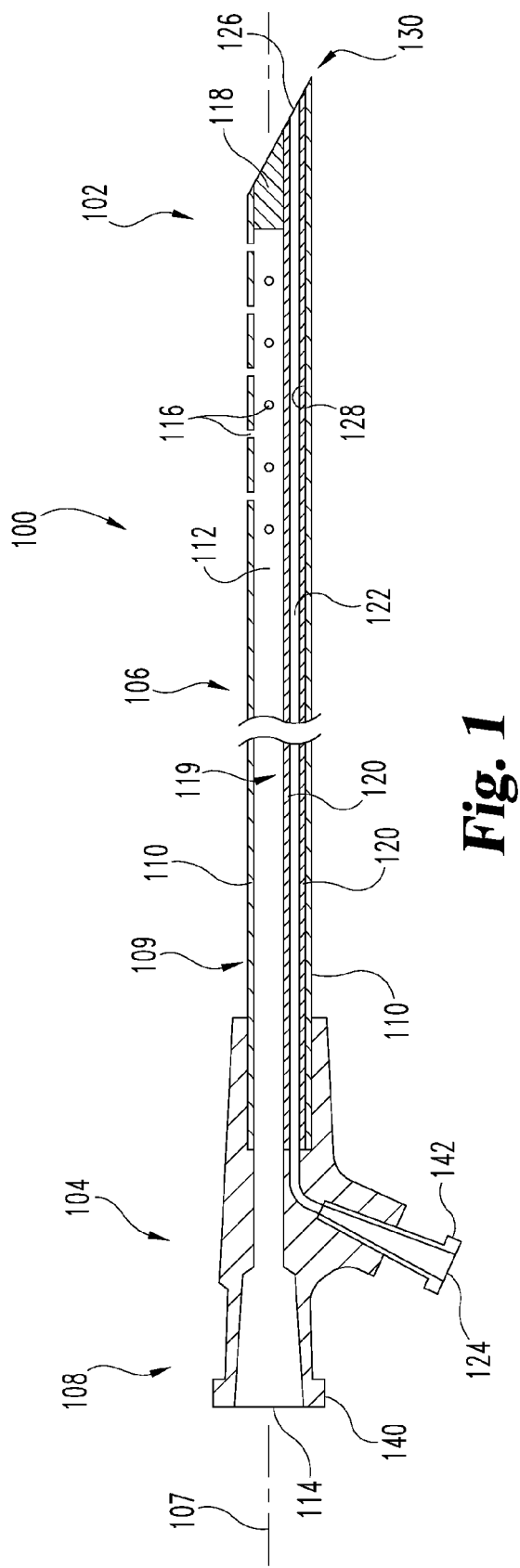
FIG. 1 is a cross-sectional, plan view of a cell-delivering needle.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, and alterations and modifications in the illustrated device, and further applications of the principles of the disclosure as illustrated therein are herein contemplated as would normally occur to one skilled in the art to which the disclosure relates.

With respect to the specification and claims, it should be noted that the singular forms "a", "an", "the", and the like include plural referents unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

The reference numerals in the following description have been organized to aid the reader in quickly identifying the drawings where various components are first shown. In particular, the drawing in which an element first appears is typically indicated by the left-most digit(s) in the corresponding reference number. For example, an element identified by a "100" series reference numeral will likely first appear in FIG. 1, an element identified by a "200" series reference numeral will likely first appear in FIG. 2, and so on.

The disclosed embodiments and variations thereof may be used to deliver bioactive agents, biologic materials such as porcine small intestinal submucosa (SIS) and/or a plurality of cells, such as stem cells, such as to locations within soft tissue anywhere in the body of a human and/or veterinary patient. For instance, the disclosed embodiments may be used to deliver cells to tissue within a patient's extremities such as a leg, or to an internal organ such as the kidney or pancreas. For simplicity, the following embodiments will be discussed with reference to the injection of a suspension of cells into tissue of a human patient. Some portions will discuss exemplary arrangements and/or methods with specific reference to a patient's leg; however, it is not intended that the present disclosure be limited to such. Similarly, reference to a cell-delivering needle is not intended to limit the device to only the delivery of cells. As mentioned, other biologic materials, such as SIS, may be delivered with the disclosed embodiments.

Figure 2:
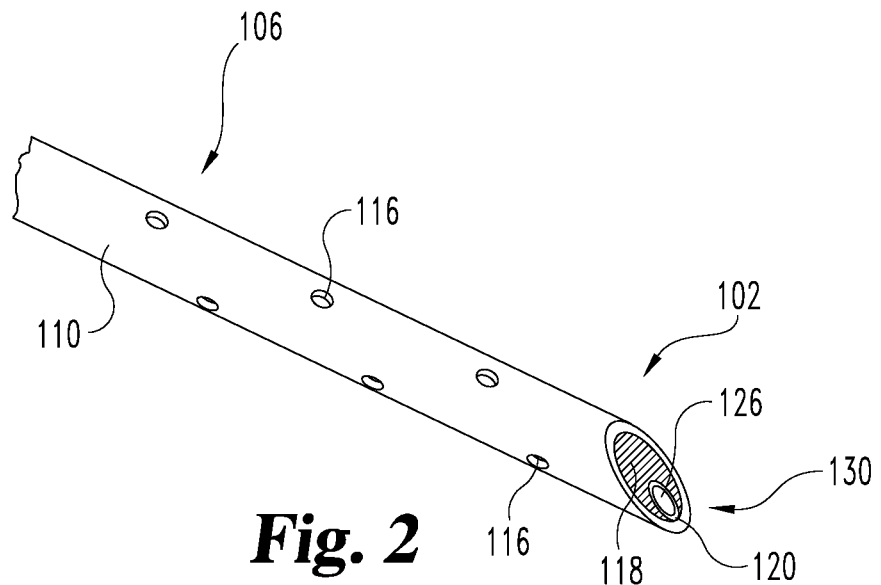
FIG. 2 is a perspective view of a distal end region of the cell-delivering needle illustrated in FIG. 1.
Figure 3:
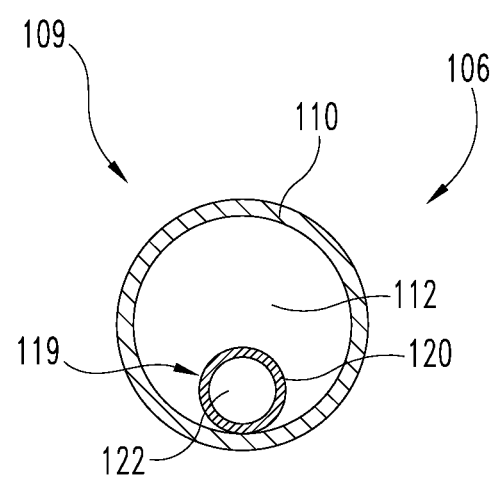
FIG. 3 is a cross-sectional view of the elongated needle body illustrated in FIG. 1.

FIGS. 1, 2 and 3 illustrate views of one embodiment of a cell-delivering needle 100. The cell-delivering needle 100 can comprise a distal end region 102, a proximal end region 104, an elongated needle body 106 and a connector 108.

The elongated needle body 106 of the cell-delivering needle 100 can comprise an outer tube 109 having a first sidewall portion 110 that defines a first lumen 112. The first lumen 112 can be in fluid-communication with a first lumen proximal opening 114 positioned in and/or near the proximal end region 104 of the cell-delivering needle 100. Additionally, the first lumen 112 can be in fluid-communication with a plurality of side ports 116 that are defined by the first sidewall portion 110 of the outer tube 109 of the elongated needle body 106. In some instances, the side ports 116 can be positioned in and/or near the distal end region 102 of the cell-delivering needle 100. A distal end of the first lumen 112 defined by the first sidewall portion 110 can contain a plug 118 arranged to block fluid flow from exiting the end of the first lumen 112.

The cell-delivering needle 100 can comprise an inner tube 119 having a second sidewall portion 120 defining a second lumen 122. The second lumen 122 can be in fluid-communication with a second lumen proximal opening 124 positioned in and/or near the proximal end region 104 of the cell-delivering needle 100. The second lumen 122 can also be in fluid-communication with a distal opening 126 positioned in and/or near the distal end region 102 of the cell-delivering needle 100. In some instances, the second sidewall portion 120 of the inner tube 119 is fixedly coupled to the first sidewall portion 110 of the outer tube 109 along a coupling surface 128. For example, the second sidewall portion 120 may be welded and/or adhesively attached to an inner wall of the first lumen 112, to name a few non-limiting examples.

In some instances the elongated needle body 106 of the cell-delivering needle 100 resembles an inner tube 119 positioned within an outer tube 109, the inner tube 119 having a maximum outer dimension smaller than the maximum outer dimension of the lumen (such as the first lumen 112) defined by the outer tube 109. As discussed above, the inner tube 119 can be fixedly attached to a wall of a lumen (such as the first lumen 112) defined by the outer tube 109. Alternatively, in some instances, the inner tube 119 is positioned within the outer tube 109 and has an annular space between an outer wall of the inner tube 119 and an inner wall of the outer tube 109. For example, the annular space may surround the inner tube 119.

The cell-delivering needle 100 may have a tissue-penetrating tip 130 positioned in the distal end region 102. The tissue-penetrating tip 130 may comprise portions of the first sidewall portion 110 and/or the second sidewall portion 120. The tissue-penetrating tip 130 may resemble any tip known to those of ordinary skill in the art to be suitable to penetrate tissue of a human and/or a veterinary patient. For example, the tissue-penetrating tip 130 may be a needle tip and/or have a single bevel and/or a triple bevel, to name just a few non-limiting examples.

The connector 108 positioned in and/or near a proximal end region 104 of the cell-delivering needle 100 may comprise a first coupling portion 140 and/or a second coupling portion 142 arranged to couple a fluid-supplying device and/or a fluid-pressurizing device, such as a syringe, to the cell-delivering needle 100. For example, the first coupling portion 140 of the first connector 108 may fluidly couple a first syringe for fluid-communication with the first lumen 112. Similarly, for example, the second coupling portion 142 of the connector 108 may fluidly couple a second syringe for fluid-communication with the second lumen 122. In some instances, the first coupling portion 140 and/or second coupling portion 142 may be arranged for the coupling of more than one lumen for fluid-communication with a fluid-supplying and/or a fluid-pressurizing device.

To illustrate the fluid-communication between the cell-delivering needle 100 and a fluid-supplying and/or a fluid-pressurizing device such as a syringe, a fluid supplied by a first syringe in fluid-communication with the cell-delivering needle 100 can travel through the connector 108, through the first lumen 112, and out of side ports 116 in a direction towards tissue adjacent to a portion of the cell-delivering needle 100, such as tissue adjacent to the elongated needle body 106. Similarly, a fluid supplied by a second syringe and/or a first syringe fluidly coupled to the second lumen 122 of the cell-delivering needle 100 can travel through the connector 108, through the second lumen 122, and out of the distal opening 126.

In some embodiments, the side ports 116 may be positioned around the periphery of a portion of the cell-delivering needle 100 such as the elongated needle body 106. For example, the side ports 116 may be positioned around the elongated needle body 106 in a repeating pattern. In some instances, the side ports 116 are helically wound around the elongated needle body 106. Alternatively or additionally, a number of the side ports 116 may be placed in a non-pattern fashion (e.g., in a random fashion) around the periphery of the elongated needle body 106 of the cell-delivering needle 100.

In some embodiments, some portions of the cell-delivering needle 100 may have more side ports 116 than other portions. For example, the distal end region 102 of the cell-delivering needle 100 may have a greater number of side ports 116 than portions of the cell-delivering needle 100 positioned proximal of the distal end region 102. Having a greater concentration, such as a greater number, of side ports 116 in a portion of the cell-delivering needle 100 may be preferred to deliver additional cells to a selected area of tissue inside of the patient.

One or more of the side ports 116 of the cell-delivering needle 100 may be of a different size and/or shape. For example, some of the side ports 116 may have a larger cross-sectional area than other side ports 116. Additionally, some of the side ports 116 may have a circular cross-section while others have an oblong cross-section.

In some embodiments the side ports 116 are positioned around the outside of the elongated needle body 106 so as to deliver a fluid suspension of cells towards tissue adjacent to the elongated needle body 106 of the cell-delivering needle 100. For example, a fluid suspension delivered from the side ports 116 and/or the first lumen 112 may travel in a radial direction away from the cell-delivering needle 100.

The side ports 116 may also be positioned in various angles with respect to a longitudinal axis of the cell-delivering needle 100 and/or a longitudinal axis of a portion of the cell-delivering needle 100, such as the longitudinal axis 107 of the elongated needle body 106. For instance, some side ports 116 may be arranged, such as by being angled, to direct a suspension of cells in a longitudinal direction (e.g., along the length of the portion of the cell-delivering needle 100) as well as in a radial direction away from the cell-delivering needle 100. Similarly, some side ports 116 may direct a suspension of cells in a direction substantially tangential to a circular cross-section of the elongated needle body 106. In some instances, multiple side ports 116 may direct a suspension of cells towards tissue positioned between the side ports 116, and in some instances some side ports 116 may direct a suspension of cells away from other side ports 116.

In some embodiments, the distal opening 126 may be positioned in and/or near the tissue-penetrating tip 130 of the cell-delivering needle 100. Additionally, the distal opening 126 may be adjacent to and/or distal of the tissue-penetrating tip 130. In some instances, the distal opening 126 and/or the second lumen 122 may be arranged to deliver a suspension of cells to tissue located adjacent to the tissue-penetrating tip 130. Additionally, the distal opening 126 and/or the second lumen 122 may be arranged so as to deliver a suspension of cells in a direction substantially along the length of the cell-delivering needle 100 and/or the elongated needle body 106. For example, a suspension of cells may travel through the second lumen 122 along the length of the elongated needle body 106 and exit the distal opening 126 in a direction along the longitudinal axis 107 of the elongated needle body 106. The distal opening 126 and/or the second lumen 122 may also be arranged to direct a suspension of cells in a direction transverse to the longitudinal axis 107 of the elongated needle body 106.

The plug 118 positioned inside of the first lumen 112 may contact portions of the second sidewall portion 120. As illustrated in FIGS. 1 and 2, the plug 118 may comprise a cylinder having a semi-circular cross-section with a recess for receiving the second sidewall portion 120 and the second lumen 122. In some embodiments, the plug 118 is arranged to block fluid flow out of the distal end of the first lumen 112. For example, a fluid may enter the first lumen 112 through the first lumen proximal opening 114 and exit through the side ports 116 but be prevented from exiting the distal end of the first lumen 112 due to the positioning of the plug 118 within the first lumen 112. Additionally, in some instances, the plug 118 can be arranged so as to allow pressurization of the first lumen 112 so as to increase the velocity and/or the pressure of a suspension of cells exiting the side ports 116, which is believed to increase the perfusion of the cells into adjacent tissue and beyond.

As illustrated in FIG. 3, the inner tube 119 may be smaller in cross-sectional area than the outer tube 109. In some instances, this can result in greater pressure loss in fluid traveling through the second lumen 122 as compared to fluid traveling through the first lumen 112. Pressure loss for fluid traveling through tubes, pipes, ducts, etc. is often discussed in terms of major loss and minor loss. Major loss is the pressure loss due to friction within the tube. Minor loss is due to changes in the velocity of the moving fluid. The major loss portion of pressure loss of a fluid traveling through a tube can be approximated by the equation:

$$\rho_{loss} = \lambda (l/d_h)(\rho v^2/2) \quad (1)$$

where
$\rho_{loss}$ = pressure loss (Pa, N/m²)
$\lambda$ = friction coefficient
$l$ = length of tube (m)
$d_h$ = hydraulic diameter (m)
$\rho$ = density of the fluid (kg/m³)
$v$ = flow velocity (m/s)

As can be understood by the approximation above, decreasing the diameter of the fluid-carrying tube will increase the pressure loss in the moving fluid. Similarly, increasing the length of fluid-carrying tube, increasing the friction coefficient (such as by increasing the surface roughness of the tube), increasing the density of the fluid, and/or increasing the velocity of the fluid moving through the tube will increase the pressure loss in the moving fluid.

In some instances it may be preferred to arrange the cell-delivering needle 100 so as to deliver a suspension of cells at a higher pressure and/or a higher velocity from one lumen and/or outlet(s) (e.g., the first lumen 112 and/or the side ports 116) than from another lumen and/or outlet(s) (e.g., the second lumen 122 and/or the distal opening 126). For example, for a sufficient perfusion of a suspension of cells into the tissue of a patient, one or more suspensions of cells may need to be delivered at a higher pressure and/or a higher velocity from the side ports 116 than from the distal opening 126. In some instances, the distal end region 102 of the cell-delivering needle 100 may be positioned adjacent to sensitive tissue such as a nerve bundle, and therefore it is desired to deliver the suspension of cells towards the sensitive tissue at a lower pressure and/or velocity than suspensions of cells being delivered to less sensitive tissue so as to decrease the likelihood of injury to the sensitive tissue. As discussed above, the length, hydraulic diameter, and/or surface roughness of a lumen may be arranged so as to achieve a desired pressure loss in the suspension of cells traveling through the lumen. Additionally, one may change the density of a fluid suspension, the velocity of a fluid suspension traveling through a lumen, and/or the type of fluid flow (laminar, transient, or turbulent) moving through the lumen to achieve a desired pressure loss. These changes may be made in addition to or as an alternative to arranging the size and shape of the sideports so as to achieve a desired pressure and/or velocity of cells exiting the sideports.

In some instances, the pressure inside of one or more lumens may be monitored. An operator may desire the pressure in a lumen to remain below a certain threshold so as to avoid damaging the cells traveling through the cell-delivering needle. Additionally, as will be appreciated by a person of ordinary skill in the art, the cell-delivering needle may be arranged so as to operate with some minimum pressure inside one or more of the lumens. For example, the sideports and/or lumens may be arranged such that a certain minimum pressure is required at a location within one or more of the lumens to achieve the desired delivery of cells from the cell-delivering needle.

In some applications, the cell-delivering needle may have built-in pressure monitoring in one or more lumens. For example, pressure sensors and/or gauges may be in communication with one or more lumens of the needle. The signals from the pressure sensors can used to adjust the volume and/or pressure of fluid being supplied to the needle (e.g., a control system for operating an actuated pressurizing device using feedback from pressure sensors). Similarly, in some embodiments, flow sensors may be used to monitor the amount of fluid flowing through one or more lumens of the needle.

The first coupling portion 140 and/or the second coupling portion 142 of the connector 108 positioned in and/or near the proximal end region 104 of the cell-delivering needle 100 may be of a standard type known and used in the medical profession. For instance the first coupling portion 140 and/or the second coupling portion 142 may be of the Luer Lock type and arranged to couple a syringe and/or other pressurizing device with the cell-delivering needle 100.

Figure 4:
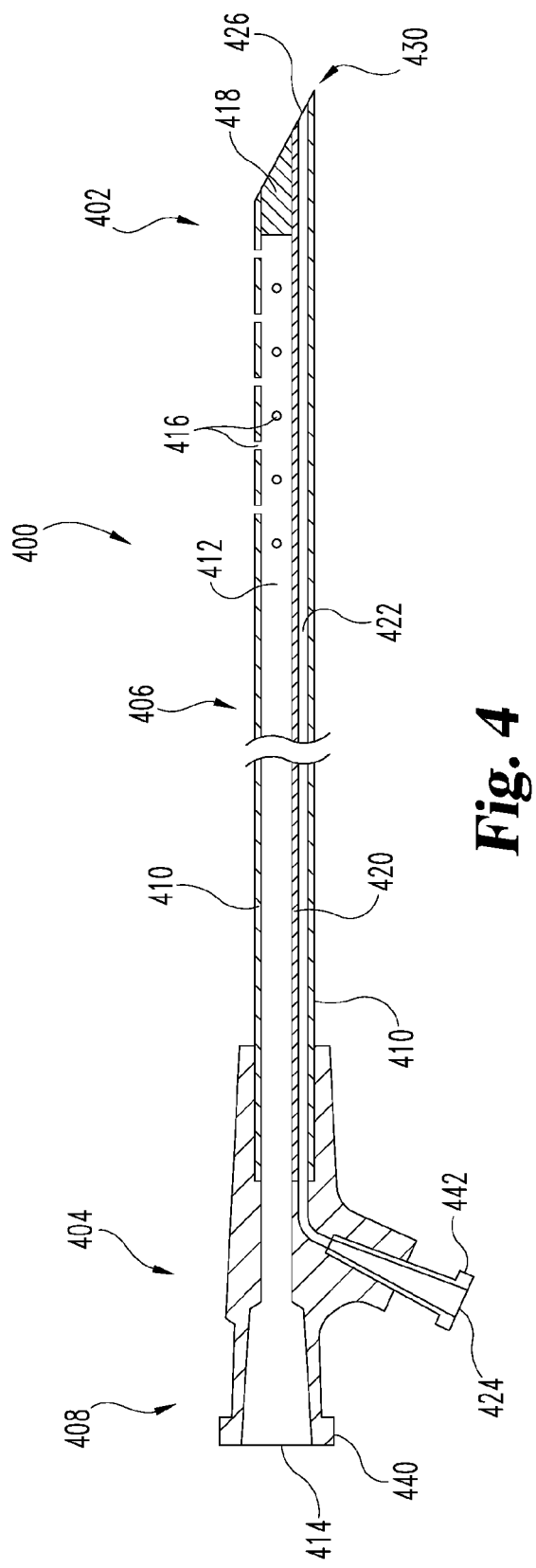
FIG. 4 is a cross-sectional, plan view of a cell-delivering needle.

FIG. 4 illustrates another embodiment of a cell-delivering needle 400. Similar to the cell-delivering needle 100 illustrated in FIGS. 1, 2, and 3, cell-delivering needle 400 comprises a distal end region 402, a proximal end region 404, an elongated needle body 406, and a connector 408 comprising a first coupling portion 440 and/or a second coupling portion 442. The cell-delivering needle 400 can comprise a first sidewall portion 410 and a second sidewall portion 420 defining a first lumen 412 and a second lumen 422. The first lumen 412 opening to a first lumen proximal opening 414 and side ports 416, and the second lumen 422 opening to a second lumen proximal opening 424 and a distal opening 426. A plug 418 can be positioned in a distal end of the first lumen 412 so as to prevent a suspension of cells from exiting a distal end of the first lumen 412, and the cell-delivering needle 400 can comprise a tissue-penetrating tip 430 positioned in the distal end region 402. In some embodiments the tissue-penetrating tip 430 and distal opening 426 of the second lumen 422 are adjacent to one another.

The second lumen 422 can be positioned within the first lumen 412, and the second lumen 422 and first lumen 412 can share a sidewall portion. For example, as illustrated in FIG. 4, the second lumen 422 may be defined by both the second sidewall portion 420 and the first sidewall portion 410. The second sidewall portion 420 of the cell-delivering needle 400 illustrated in FIG. 4 in some instances may comprise an additional portion of the elongated needle body 406 such as an extension from the first sidewall portion 410 of the cell-delivering needle 400.

Figure 5:
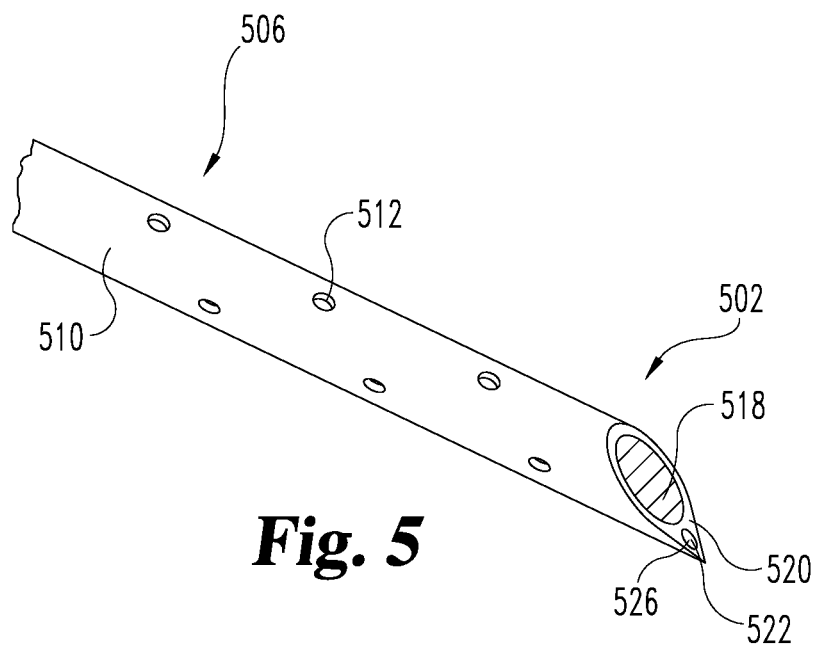
FIG. 5 is a perspective view of a distal end region of the cell-delivering needle illustrated in FIG. 4.

FIG. 5 illustrates a perspective view of one embodiment of a cell-delivering needle such as that illustrated in FIG. 4. In this illustration, the second sidewall portion 520 of the elongated needle body 506 is arranged such that the first lumen 512 does not extend substantially around the second lumen 522. As is shown in the figure, the plug 518 in the distal end region 502 does not have a recess for the second sidewall portion 520 and/or the second lumen 522. The first lumen 512, the second lumen 522, the plug 518, and/or the distal opening 526 can have circular cross-sections. In some instances, the second sidewall portion 520 can comprise extensions of the first sidewall portion 510.

Figure 6:
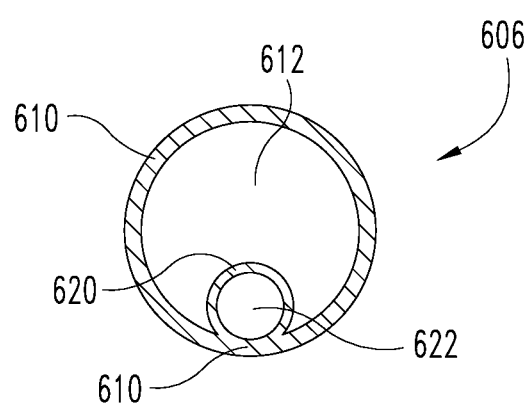
FIG. 6 is a cross-sectional view of the elongated needle body illustrated in FIG. 4.

FIG. 6 illustrates a cross-sectional view of an elongated needle body 606 of another embodiment of a cell-delivering needle, such as the cell-delivering needle 400 illustrated in FIG. 4. In this illustration, the second side wall portion 620 forms a loop within the first lumen 612 defined by the first sidewall portion 610. The second lumen 622 can be positioned inside of the first lumen 612 and defined by both the second sidewall portion 620 and the first sidewall portion 610.

As illustrated in this and other embodiments, the nested placement of the second lumen (e.g., second lumen 422) within the first lumen (e.g., first lumen 412) and/or sharing of sidewalls between the second and/or first lumen can provide a number of benefits. For instance, positioning one lumen inside of the other can allow for a smaller maximum outer dimension for the cell-delivering needle. In embodiments that share sidewall portions, the overall needle cross-sectional area may be reduced, as compared to embodiments that do not share sidewall portions, while maintaining the cross-sectional areas of the lumens. Additionally, positioning the second lumen inside of the first lumen and/or along a sidewall thereof can allow for the positioning of the distal opening closer to the tissue-penetrating tip of the cell-delivering needle.

Other benefits of positioning the second lumen within the first lumen and/or the sharing of sidewalls therewith will be apparent to those of ordinary skill in the art. For example, the sharing of sidewalls between lumens can decrease the amount of material necessary to form the elongated needle body and/or both lumens.

Figure 7:
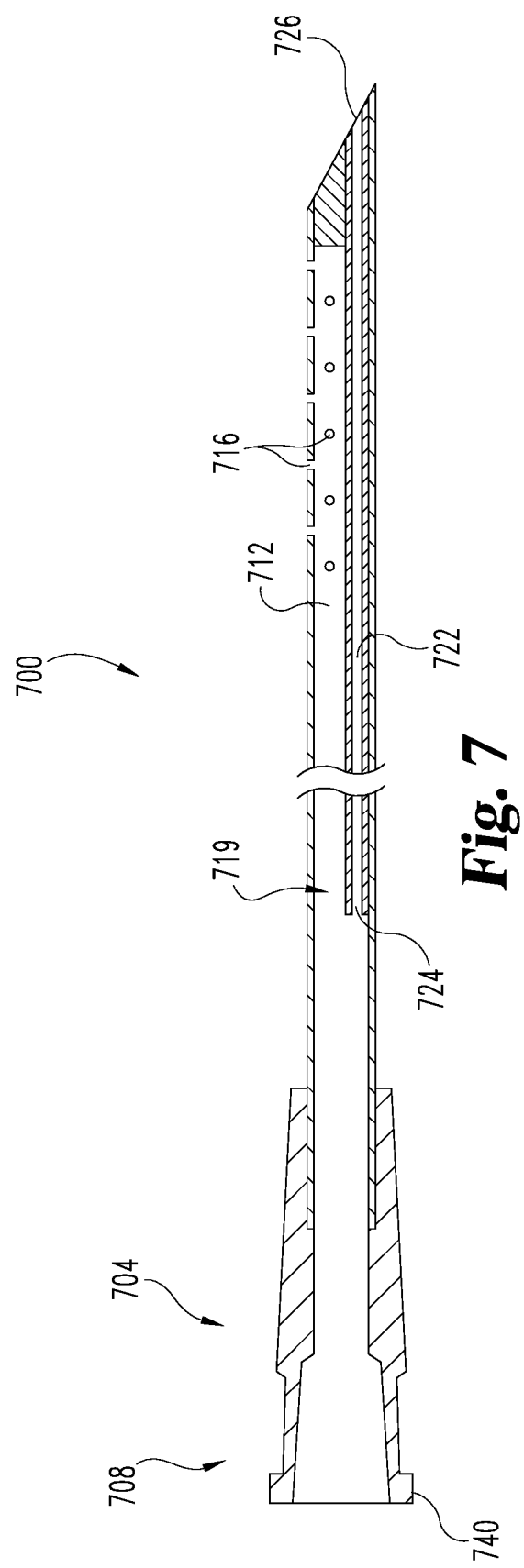
FIG. 7 is a cross-sectional, plan view of a cell-delivering needle.
Figure 8:
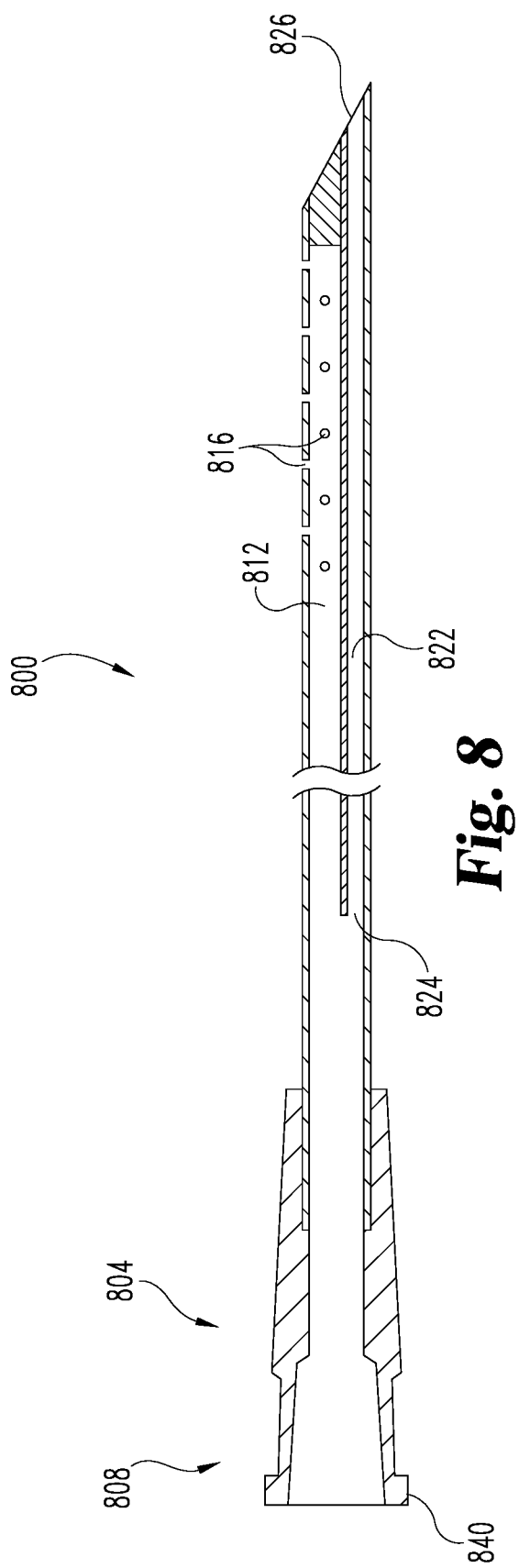
FIG. 8 is a cross-sectional, plan view of a cell-delivering needle.

FIGS. 7 and 8 illustrate additional embodiments of a cell-delivering needle. In these embodiments, the second lumen proximal opening 724, 824 is in fluid communication with the first lumen 712, 812. This arrangement can allow for a single fluid-supplying device and/or fluid-pressurizing device to provide a suspension of cells to the first lumen 712, 812 and the second lumen 722, 822. In some instances a suspension of cells is provided to the first lumen 712, 812 and the second lumen 722, 822 simultaneously.

This arrangement can also allow for a suspension of cells to be delivered from the distal opening 726, 826 at a pressure lower than a suspension of cells delivered from the side ports 716, 816. In some instances the hydraulic diameter of the second lumen 722, 822 may be less than the hydraulic diameter of the first lumen 712, 812 and cause a greater pressure loss greater in the second lumen 722, 822 than in the first lumen 712, 812. For example, the inner tube 719 can have a maximum outer dimension smaller than the maximum outer dimension of the first lumen 712 and can be arranged so as to deliver a suspension of cells from the distal opening 726 at a pressure lower than a suspension of cells delivered from one or more side ports 716. Additionally, the side ports 716, 816 and/or the distal opening 726, 826 may be arranged so as to provide additional pressure loss (minor losses) to the fluid suspension of cells being delivered from the side ports 716, 816 and/or the distal opening 726, 826.

The cell-delivering needle 700, 800 can have a connector 708, 808 positioned at a proximal end region 704, 804 of the cell-delivering needle 700, 800. The connector 708, 808 can have a coupling portion 740, 840 arranged to couple a fluid-supplying device and/or fluid-pressurizing device to the cell-delivering needle 700, 800. The connector 708, 808 and/or the coupling portion 740, 840 can be arranged to fluidly-couple the fluid-supplying device and/or fluid-pressurizing device to the first lumen 712, 812 and the second lumen 722, 822.

Figure 9:
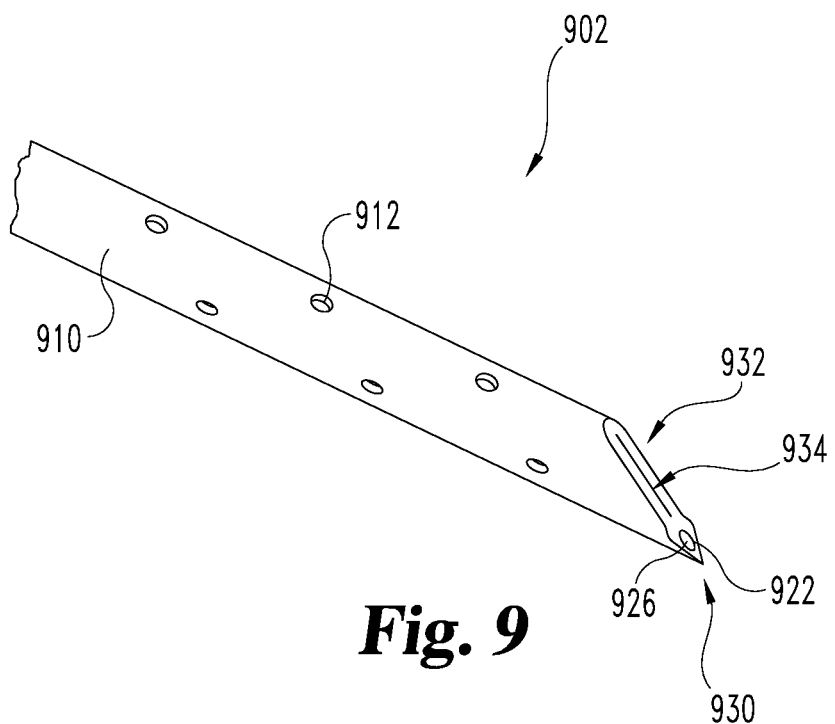
FIG. 9 is a perspective view of a distal end region of a cell-delivering needle.

FIG. 9 illustrates a perspective view of a distal end region 902 of a cell-delivering needle. A first lumen 912 defined by the first sidewall portion 910 terminates in a closed distal end 932 in a beveled region 934 adjacent to a tissue-penetrating tip 930. In some instances, the distal end of the first lumen 912 is closed by a crimped portion of the first sidewall portion 910 in the beveled region 934. In some embodiments the distal opening 926 of the second lumen 922 is positioned adjacent to the tissue-penetrating tip 930 and the closed distal end 932 of the first lumen 912.

Figure 10:
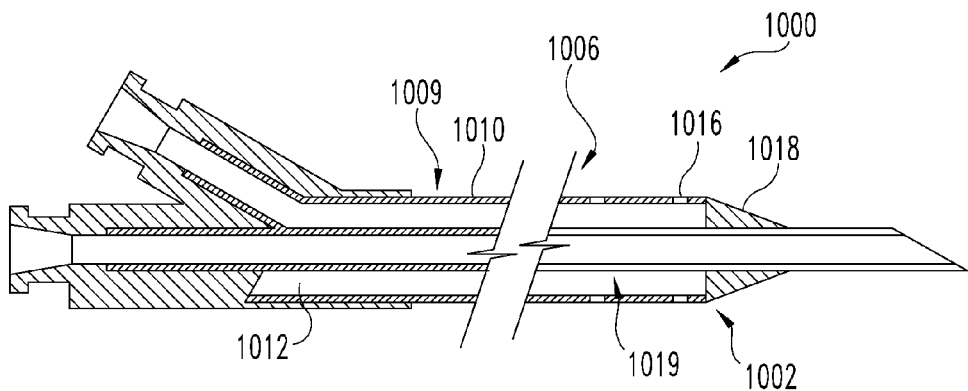
FIG. 10 is a cross-sectional, plan view of a cell-delivering needle.
Figure 11:
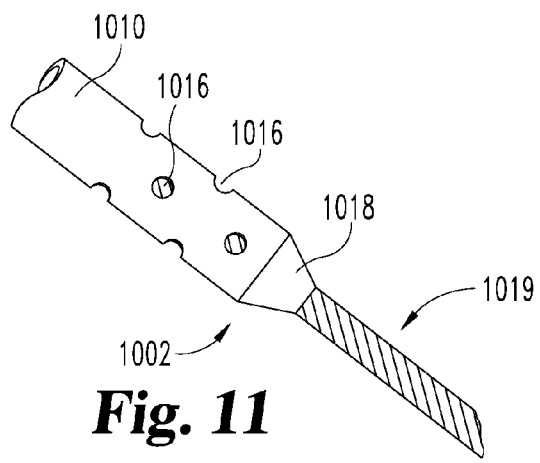
FIG. 11 is a perspective view of the cell-delivering needle illustrated in FIG. 10.
Figure 12:
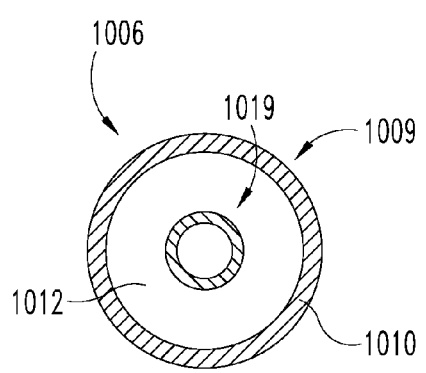
FIG. 12 is a cross-sectional view of the elongated needle body illustrated in FIG. 10.

FIGS. 10-12 illustrate another embodiment of a cell-delivering needle. Similar to some of the embodiments disclosed above, the cell-delivering needle 1000 has an elongated needle body 1006 and comprises an outer tube 1009 and an inner tube 1019, the outer tube 1009 having a first sidewall portion 1010 that defines a plurality of side-ports 1016 spaced around the circumference of the outer tube 1009. In some instances, the inner tube 1019 is positioned concentrically within the outer tube 1009 so as to have a co-axial arrangement. A plug 1018 is positioned around the circumference of the inner tube 1019 to seal the distal end region 1002 of the first lumen 1012.

Figure 13:
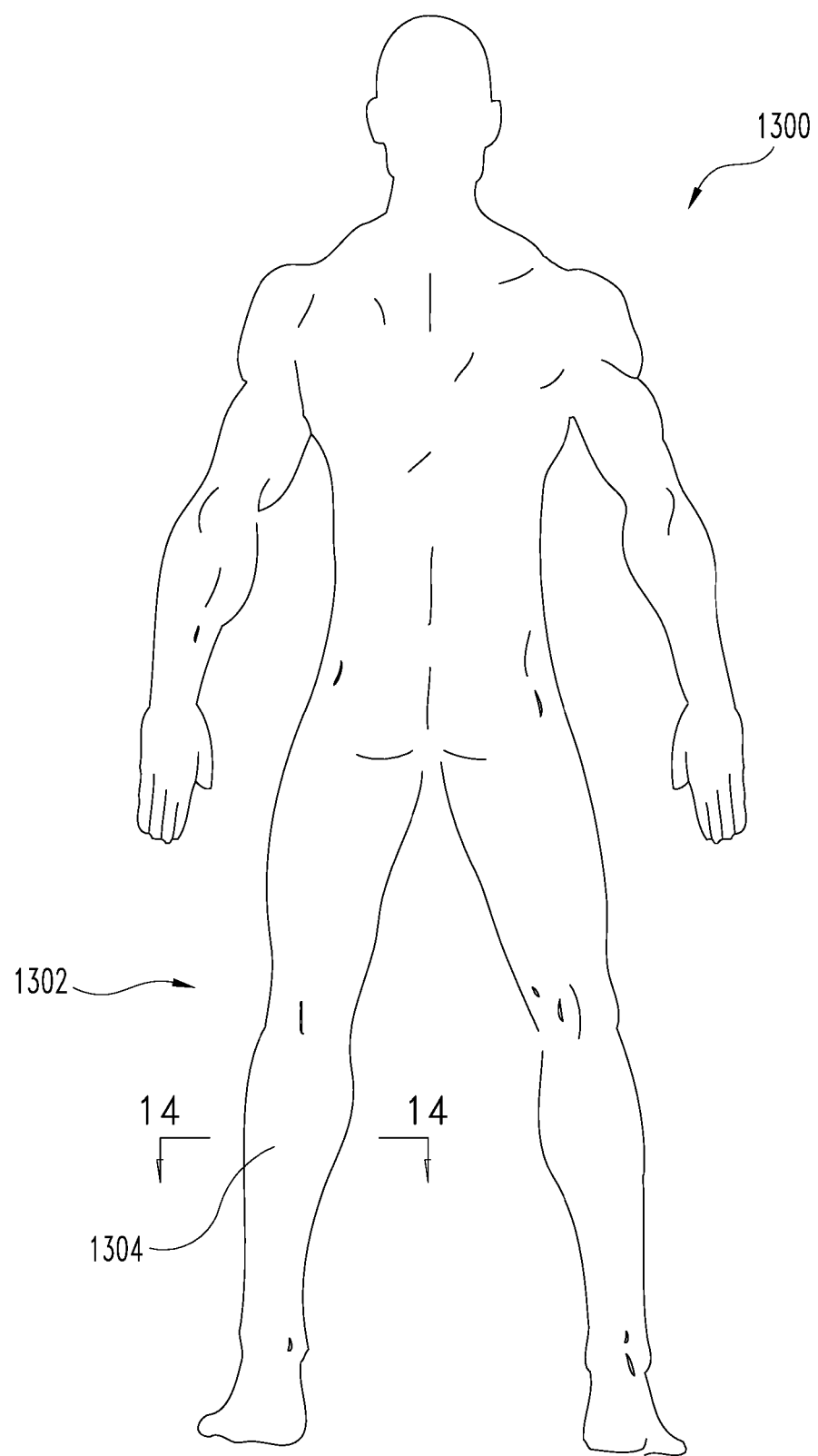
FIG. 13 illustrates the body of a patient.

FIG. 13 illustrates a plan view of the body of a patient 1300. The disclosed embodiments of cell-delivering needles may be used to deliver a plurality of cells and/or a biologic agent to organs or soft tissue anywhere in the body. In some instances a cell-delivering needle may be used to treat tissue positioned inside of a patient's leg 1302. More specifically in some instances the cell delivering needle is used to treat tissue positioned within the calf portion 1304 of the leg 1302.

The various embodiments of the cell-delivering needle and portions thereof disclosed above may be constructed from materials such as those known in the art to be used for construction of needles and/or cannulas. For example, the elongated needle body and portions thereof may be formed from materials commonly used to manufacture needles and/or cannulas, such as stainless and/or surgical steel to name a few non-limiting examples. Portions of the cell-delivering needle, such as the connector, may also be formed of polymer materials such as polypropylene and/or polyethylene, just to name a few non-limiting examples.

Additionally, the various embodiments of the cell-delivering needle and portions disclosed above may be formed by any method known by those of ordinary skill in the art. For example, the cell-delivering needle 100 illustrated in FIG. 1 may be constructed by welding portions of the inner tube 119 to the outer tube 109. Additionally or alternatively, portions of the inner tube 119 and/or outer tube 109 may be affixed relative to one another by the connector 108. In some embodiments, the plug 118 in the first lumen 112 fixedly attaches the outer tube 109 to the inner tube 119. Other methods known by those of ordinary skill in the art used to construct multi-lumen needles, such as swaging one tube inside of another tube, can be used as well.

Method of Use

Various embodiments of the present disclosure are arranged to deliver a suspension of cells to tissue within a patient's body. In some instances, the present disclosure provides embodiments arranged to deliver a suspension of cells to tissue, such as muscle, positioned at various depths beneath the surface of the patient's skin. Exemplary methods of delivering cells into an extended volume of tissue in a patient will now be discussed. Some of the disclosed embodiments will be used to illustrate methods of delivering cells into the tissue within a leg of a patient, but no limitation to such is intended.

Figure 14:
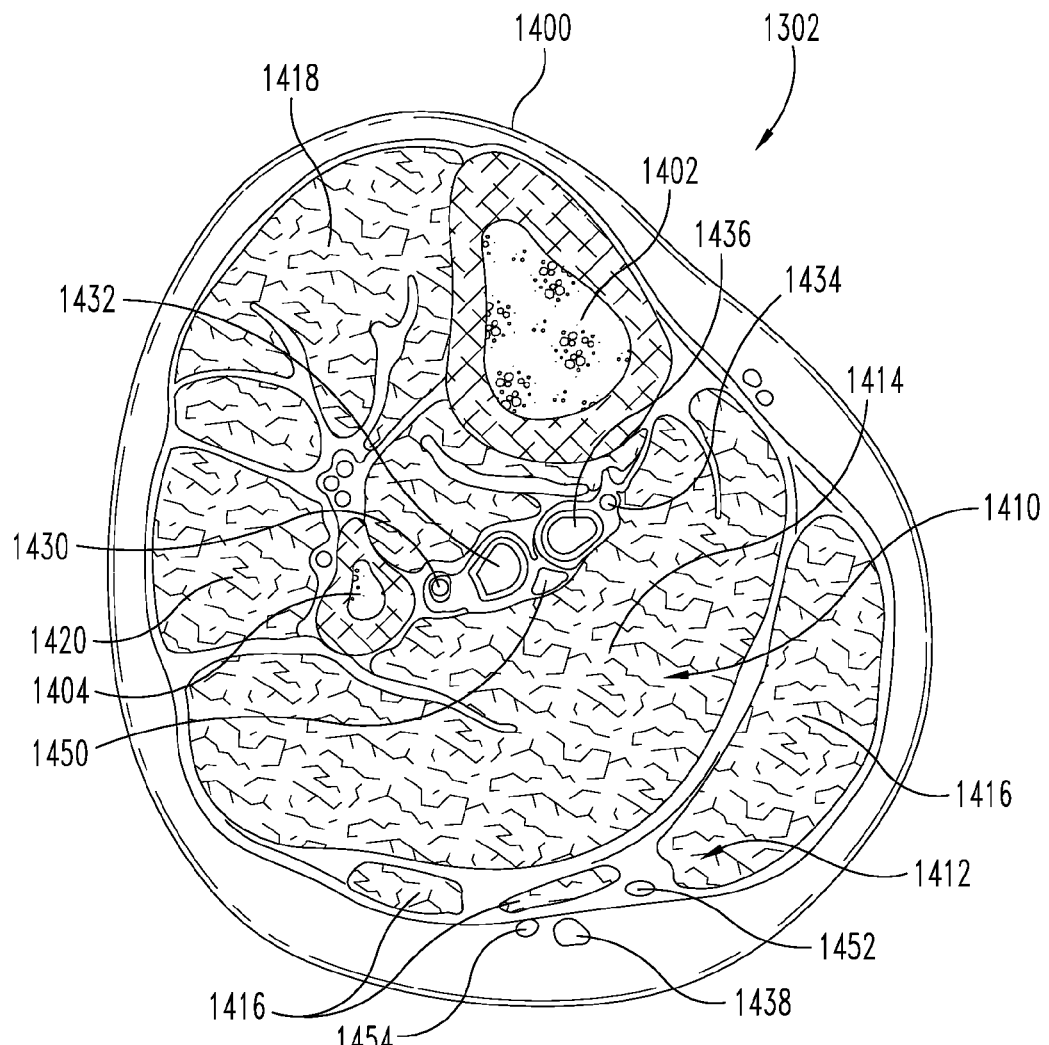
FIG. 14 illustrates a cross-sectional view of a leg of a patient.

FIG. 14 illustrates a cross-sectional view of the calf portion 1304 of the leg 1302 of the body of a patient 1300. The skin 1400 of the leg 1302 encompasses the tibia 1402, and the fibula 1404, as well as muscle tissue, vessels, and nerves.

When discussing the muscles of the leg 1302, the muscles are often divided into deep layer muscle 1410 and superficial layer muscle 1412. The deep layer muscle 1410 resides further beneath the surface of the skin 1400 than the superficial layer muscle 1412. For example, the soleus muscle 1414 is a deep layer muscle 1410, and the gastrocnemius muscle 1416 is a superficial layer muscle 1412. Both the soleus muscle 1414 and the gastrocnemius muscle 1416 are located posteriorly of the tibia 1402 and the fibula 1404. In the anterior portion of the leg 1302 is the tibialis anterior muscle 1418 that is located mostly laterally of the tibia 1402. Posteriorly of the tibialis anterior muscle 1418 and laterally of the fibula 1404 is the fibularis (aka: the peroneus) brevis and longus muscles 1420.

There are a number of vessels located in the calf portion 1304 of the leg 1302. Positioned between the solues muscle 1414 and the tibialis anterior muscle 1418 are the peroneal artery 1430, the peroneal vein 1432, the posterior tibial artery 1434, and the posterior tibial vein 1436. The leg 1302 also has the small sapheous vein 1438 that is located in the superficial posterior portion of the leg 1302.

Also of note for the present disclosure are various nerves located in the calf portion 1304 of the leg 1302. The tibial nerve 1450 is positioned between the soleus muscle 1414 and the tibialis anterior muscle 1418. In the superficial posterior portion of the leg 1302 are the medial cutaneous nerve 1452 and the lateral cutaneous nerve 1454.

Figure 15:
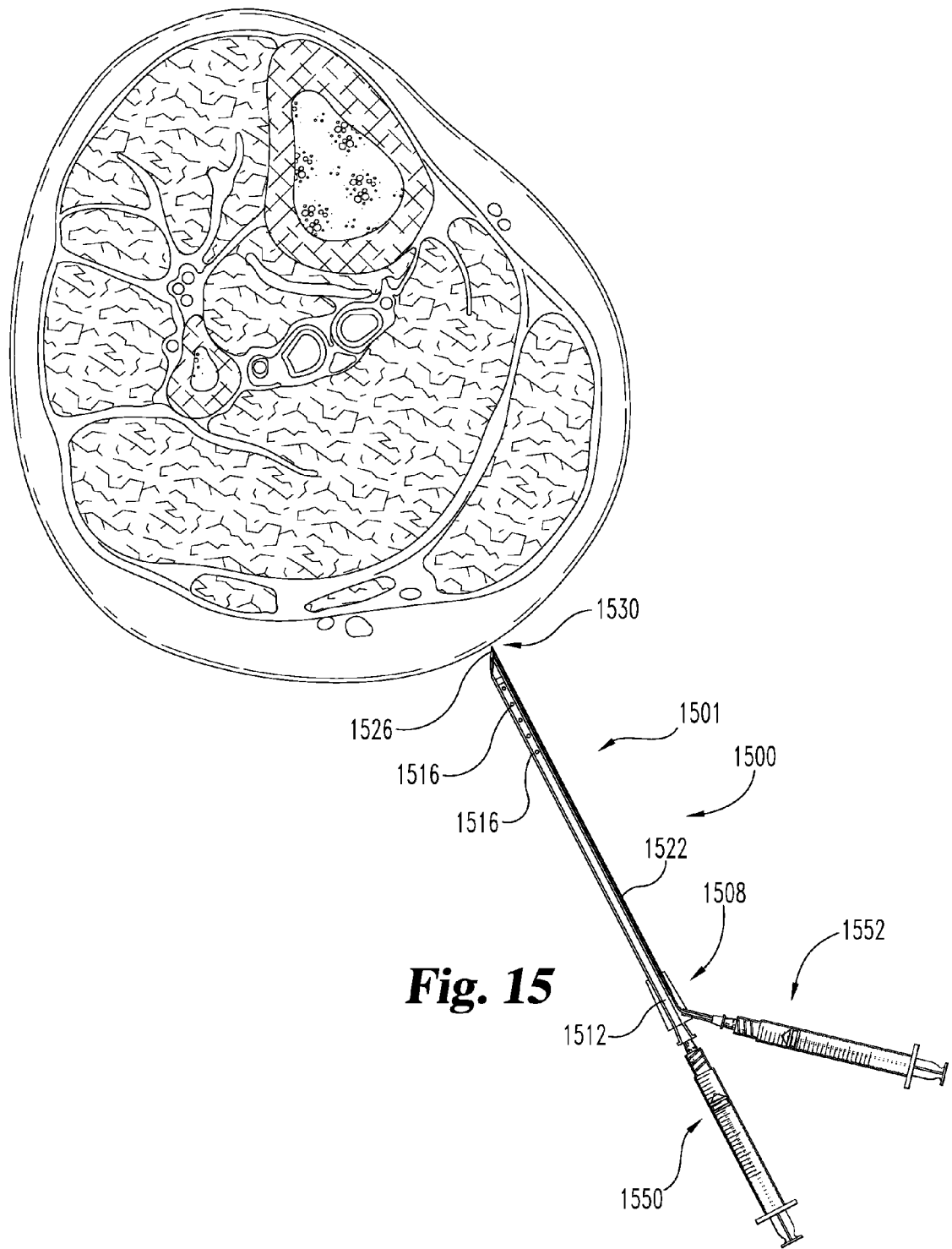
FIG. 15 illustrates a cross-sectional view of a leg of a patient with a cell-delivering needle assembly being brought into proximity therewith.

FIG. 15 illustrates an exemplary cell-delivering needle assembly 1500. The cell-delivering needle assembly 1500 can comprise a cell-delivering needle 1501 and a first syringe 1550 and/or a second syringe 1552. The cell-delivering needle 1501 can also have a connector 1508 for coupling the cell-delivering needle 1501 to the first syringe 1550 and/or the second syringe 1552. The connector 1508 can allow the fluid communication of the first lumen 1512 and side ports 1516 with the first syringe 1550 and the fluid communication of the second lumen 1522 and distal opening 1526 with the second syringe 1552.

As illustrated in FIG. 15, the exemplary cell-delivering needle assembly 1500 is positioned relative to the leg 1302 of a patient with the tissue-penetrating tip 1530 positioned adjacent to the skin 1400 of a leg 1302. The cell-delivering needle assembly 1500 may be inserted in a variety of directions towards a deep layer muscle 1410. For example, the cell-delivering needle assembly 1500 may be inserted into a posterior portion of the leg 1302 along a posterior to anterior direction. Alternatively, the cell-delivering needle assembly 1500 may be inserted into an anterior portion of the leg 1302 along a anterior to posterior direction.

The cell-delivering needle assembly 1500 can be advanced in a posterior to anterior direction through the skin 1400 of the patient medially of the medial cutaneous nerve 1452. After penetrating the skin 1400, an operator can check the positioning of the distal end region (such as the tissue-penetrating tip 1530) of the cell-delivering needle 1501. For example, the operator may check whether the tissue-penetrating tip 1530 of the cell-delivering needle 1501 has penetrated a blood vessel such as the small saphenous vein 1438 in the superficial posterior portion of the leg 1302. One way an operator may check is by applying a negative pressure, by use of the syringe, to the first lumen 1512 and/or second lumen 1522. If the operator observes flashback (i.e., a flash of blood that is observed when a needle punctures a blood vessel) then the tissue-penetrating tip 1530 has punctured a blood vessel. Alternatively or additionally, imaging such as x-ray and/or ultrasound may be used to confirm the proper positioning of the distal end region of the cell-delivering needle 1501.

The cell-delivering needle 1501 portion of the cell-delivering needle assembly 1500 may then be advanced through the gastrocnemius muscle 1416 and the soleus muscle 1414 following a path towards the tibial nerve 1450. In some instances, the cell-delivering needle 1501 is advanced until the tissue-penetrating tip 1530 is positioned posteriorly of the tibial nerve 1450. Additionally, as the cell-delivering needle 1501 is advanced, a suspension of cells may be delivered through the side ports 1516 and/or the distal opening 1526 of the cell-delivering needle 1501.

Figure 16:
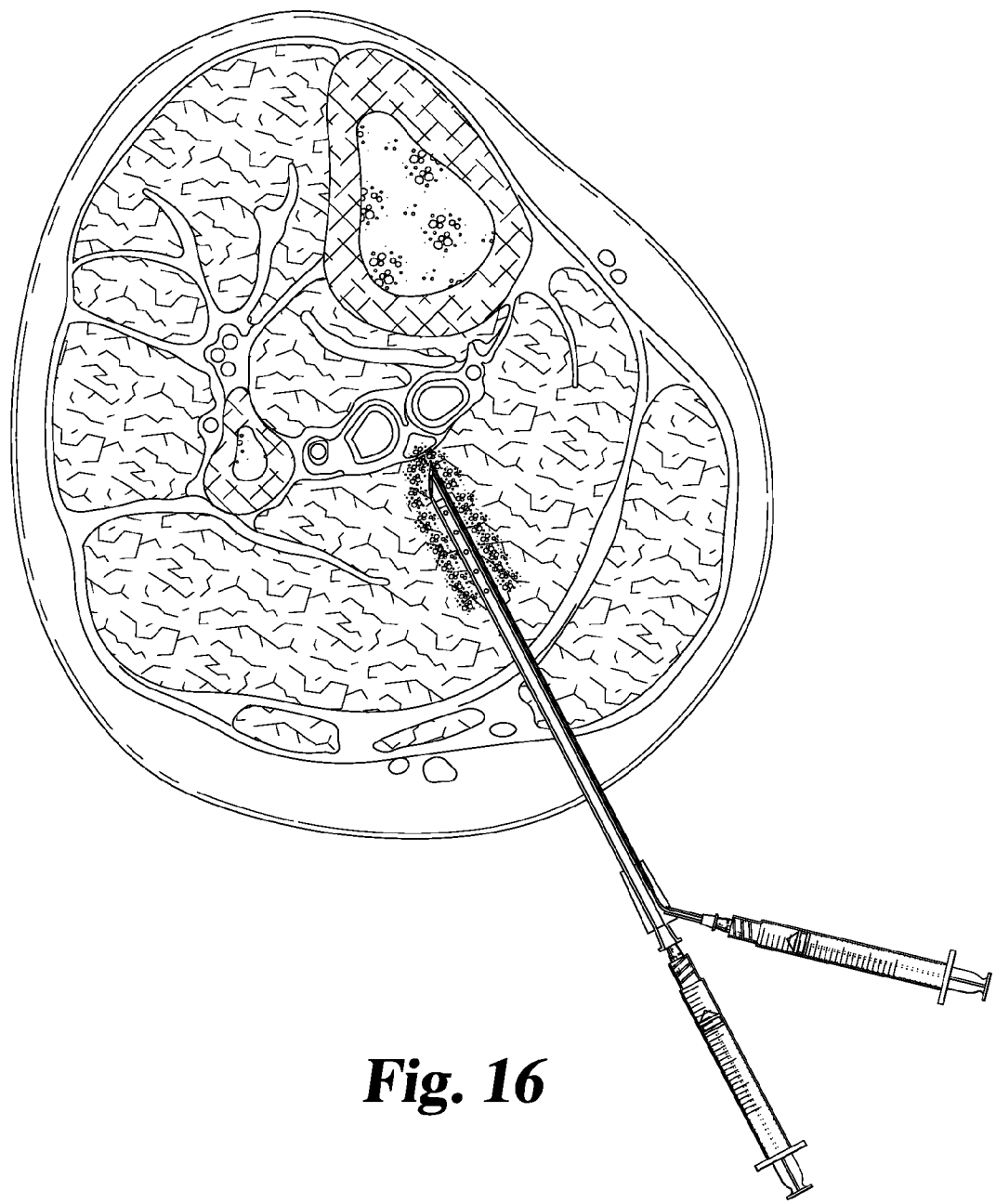
FIG. 16 illustrates the insertion of a cell-delivering needle assembly into a leg of a patient and the delivery of cells.
Figure 17:
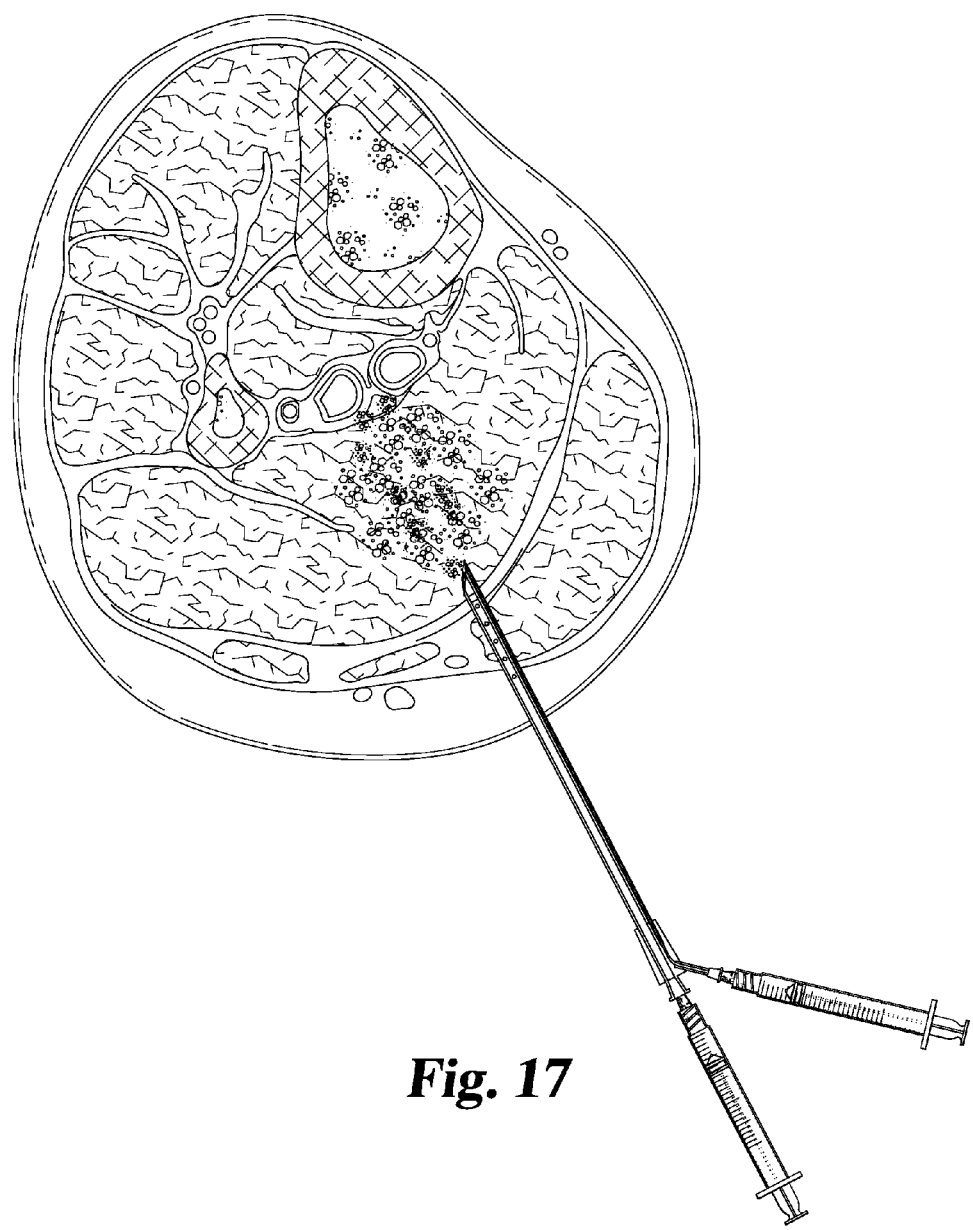
FIG. 17 illustrates withdrawing a cell-delivering needle assembly from a leg of a patient.

The cell-delivering needle 1501 is advanced to a desired position in the tissue, such as that illustrated in FIG. 16. In some instances, the distal opening 1526 and/or side ports 1516 may become clogged with tissue, such as skin and/or muscle tissue. To check the patency of the side ports 1516 and/or the distal opening 1526, the user may apply negative pressure to the first lumen 1512 and/or second lumen 1522 such as by use of the first and/or second syringe 1550, 1552.

After the cell-delivering needle 1501 is in position, a suspension of cells can be delivered. A suspension of cells can be delivered through the side ports 1516 and/or the distal opening 1526 of the cell-delivering needle 1501. Cells can be delivered from the side ports 1516 into deep layer muscle 1410 and/or superficial layer muscle 1412. For example, cells may be delivered into the soleus muscle 1414, and/or the gastrocnemius muscle 1416. In some embodiments, cells delivered from the side ports 1516 perfuse into the tissue adjacent to the side ports 1516 and beyond the needle tract.

In some embodiments, a first suspension of cells is delivered through the first lumen 1512 and the side ports 1516 and a second suspension of cells is delivered through the second lumen 1522 and the distal opening 1526. In some embodiments, the suspensions delivered through the first and second lumens 1512, 1522 and the side ports 1516 and distal opening 1526 are the same.

Additionally or alternatively, cells can be delivered from the distal opening 1526 towards the tibial nerve 1450, the peroneal artery/vein 1430, 1432, and/or the posterior tibial artery/vein 1434, 1436. In some instances, it is preferred to deliver a plurality of cells towards the tibial nerve 1450 so as to promote innervation. Additionally, delivering cells near the peroneal artery/vein 1430, 1432 and/or the posterior tibial artery/vein 1434, 1436 may promote angiogenesis (i.e., vessel formation) in tissue, such as the soleus muscle 1414.

After a suspension of cells has been delivered from the side ports 1516 and/or the distal opening 1526, the cell-delivering needle 1501 may be withdrawn. As the cell-delivering needle 1501 is being withdrawn, additional suspensions of cells may be delivered from the side ports 1516 and/or the distal opening 1526. For example, an additional suspension of cells may be delivered from the distal opening 1526 and/or the side ports 1516 into the needle tract.

The cell-delivering needle 1501 may also be flushed with a saline solution before, during and or after the various stages disclosed above. For example, the cell-delivering needle 1501 may be flushed with saline before the tissue-penetrating tip 1530 is inserted into tissue. Similarly, the cell-delivering needle 1501 may be flushed with saline to transport cells through and/or from the first lumen 1512, second lumen 1522, side ports 1516, and/or distal opening 1526.

While the disclosure has been illustrated and described in detail in the drawings and foregoing description, the same is to be considered as illustrative and not restrictive in character, it being understood that the preferred embodiment has been shown and described and that all changes and modifications that come within the spirit of the disclosure are desired to be protected. It will be evident from the specification that aspects or features discussed in one context or embodiment will be applicable in other contexts or embodiments. The following numbered clauses set out specific embodiments that may be useful in understanding the present invention:

1. A method of delivering a biologic material into an extended volume of tissue of a patient, comprising:
    advancing a distal end region of a biologic-material-delivering needle having an elongated body defining a first lumen, a second lumen, a plurality of side ports associated with said first lumen, an end port associated with said second lumen, and a tissue-penetrating tip through the skin of the patient;
    passing a first suspension of biologic material through said first lumen and out of said side ports associated with said first lumen to release a biologic material from said side ports towards tissue adjacent to said elongated body; and
    passing a second suspension of biologic material through said second lumen and out of said end port associated with said second lumen to release a biologic material from said end port into tissue of the patient.

2. The method of clause 1, wherein:
said biologic material comprises cells.

3. The method of clause 1, wherein:
said second lumen is defined by a second elongate body positioned within said first lumen and said second elongate body is surrounded by an annular space.

4. The method of clause 1, wherein:
said second lumen is defined by a second elongate body positioned within said first lumen and fixedly coupled to a wall thereof.

5. The method of clause 1, further comprising:
withdrawing said biologic-material-delivering needle while passing a suspension of biologic material into the biologic-material-delivering needle tract.

6. The method of clause 1, wherein:
said plurality of side ports are positioned around the periphery of the elongated body.

7. The method of clause 5, wherein:
passing a suspension of biologic material into the biologic material-delivery needle that comprises passing a suspension of biologic material through said second lumen and out of said end port associated with said second lumen.

8. The method of clause 7, further comprising:
passing a suspension of biologic material through said first lumen and out of said side ports associated with said first lumen while withdrawing said biologic-material-delivering needle.

9. The method clause 1, further comprising:
connecting a first injecting member to a first connecting member of said biologic-material-delivering needle for fluid communication with said first lumen.

10. The method of clause 9, further comprising:
connecting a second injecting member to a second connector of said biologic-material-delivering needle for fluid communication with said second lumen.

11. The method of clause 1, wherein:
passing a first suspension of biologic material through said first lumen and out of said side ports associated with said first lumen occurs at a higher pressure than said passing a second suspension of biologic material through said second lumen and out of said end port associated with said second lumen.

12. The method of clause 1, wherein:
said second suspension of biologic material passing through said second lumen and out of said distal opening has a greater pressure loss than said first suspension of biologic material passing through said first lumen and out of said ports.

13. A needle, comprising:
a needle body having a proximal end region, a distal end region, and a sidewall;
said needle body defining a first lumen extending from said proximal end region to said distal end region;
said first lumen terminating in a closed distal end and communicating with a plurality of ports defined by said sidewall;
said needle body defining a second lumen extending from said proximal end region to said distal end region and communicating with a distal opening in said distal end region; and
said distal end region having a tissue-penetrating tip.

14. The needle of clause 13, wherein:
said first lumen and said second lumen are fixedly positioned to one another.

15. The needle of clause 13, wherein:
said ports are positioned around the periphery of said needle body.

16. The needle of clause 13, wherein:
said ports have a cross-sectional area that is smaller than a cross-sectional area of said distal opening.

17. The needle of clause 13, wherein:
said second lumen has a cross-sectional area that is smaller than a cross-sectional area of said first lumen.

18. The needle clause 13, wherein:
said second lumen is positioned within said first lumen.

19. The needle of clause 18, wherein:
said second lumen is surrounded by an annular space.

20. The needle of clause 13, wherein:
a distal end of said second lumen extends beyond a distal end of said first lumen.

21. The needle of clause 13, further comprising:
a plug closing the distal end of said first lumen.

22. A fluid delivering needle, comprising:
a needle body having a proximal end region, a distal end region, a first elongated body, and a second elongated body;
said first elongated body having a sidewall defining a first lumen extending from said proximal end region to said distal end region;
said first lumen terminating in a closed distal end and communicating with a plurality of ports defined by said sidewall and positioned around the periphery of said first elongated body;
said second elongated body positioned within said first lumen and fixedly coupled to a wall thereof;
said second elongated body defining a second lumen extending from said proximal end region to said distal end region and communicating with a distal opening in said distal end region; and
said distal end region of said needle body having a tissue-penetrating needle tip.

What is claimed is:

1. A needle, comprising:
a needle body having a proximal end region, a distal end region, and a sidewall;
said needle body defining a first lumen extending from said proximal end region to said distal end region;
said first lumen terminating in a closed distal end and communicating with a plurality of ports defined by said sidewall;
said needle body defining a second lumen extending from said proximal end region to said distal end region and communicating with a distal opening in said distal end region; and
said distal end region having a tissue-penetrating tip;
wherein said second lumen is positioned within said first lumen.

2. The needle of claim 1, wherein:
said first lumen and said second lumen are fixedly positioned to one another.

3. The needle of claim 1, wherein:
said ports are positioned around the periphery of said needle body.

4. The needle of claim 1, wherein:
said ports have a cross-sectional area that is smaller than a cross-sectional area of said distal opening;
wherein said cross-sectional area of a port is measured in a plane perpendicular to a direction of fluid flow through said port; and
wherein said cross-sectional area of said distal opening is measured in a plane perpendicular to a direction of fluid flow through said distal opening.

5. The needle of claim 1, wherein:
said second lumen has a hydraulic diameter that is smaller than a hydraulic diameter of said first lumen.
6. The needle of claim 1, wherein:
said second lumen is surrounded by an annular space.
7. The needle of claim 1, wherein:
a distal end of said second lumen extends beyond a distal end of said first lumen.
8. The needle of claim 1, further comprising:
a plug closing the distal end of said first lumen.
9. The needle of claim 1, wherein:
said plurality of ports are longitudinally spaced along a length of said needle body.
10. The needle of claim 1, further comprising:
a connector in the proximal end region, the connector having a first coupling portion and a second coupling portion;
said first coupling portion arranged to fluidly couple a first syringe with said first lumen; and
said second coupling portion arranged to fluidly couple a second syringe with said second lumen.
11. The needle of claim 1, wherein:
said plurality of side ports includes one or more side ports of different size.
12. The needle of claim 1, wherein:
said needle body is arrange to deliver fluid from said plurality of ports at a higher velocity than fluid exiting said distal opening.
13. The needle of claim 1, wherein said plurality of ports open directly to said first lumen.
14. A fluid delivering needle, comprising:
a needle body having a proximal end region, a distal end region, a first elongated body, and a second elongated body;
said first elongated body having a sidewall defining a first lumen extending from said proximal end region to said distal end region;
said first lumen terminating in a closed distal end and communicating with a plurality of ports defined by said sidewall and positioned around the periphery of said first elongated body;
said second elongated body positioned within said first lumen and fixedly coupled to a wall thereof;
said second elongated body defining a second lumen extending from said proximal end region to said distal end region and communicating with a distal opening in said distal end region; and
said distal end region of said needle body having a tissue-penetrating needle tip.
15. The needle of claim 14, wherein:
said plurality of ports are longitudinally spaced along a length of said needle body.
16. The needle of claim 14, further comprising:
a connector in the proximal end region, the connector having a first coupling portion and a second coupling portion;
said first coupling portion arranged to fluidly couple a first syringe with said first lumen; and
said second coupling portion arranged to fluidly couple a second syringe with said second lumen.
17. The needle of claim 14, wherein:
said plurality of side ports includes one or more side ports different size.
18. The needle of claim 14, wherein:
said needle body is arranged to deliver fluid from said plurality of ports at a higher velocity than fluid exiting said distal opening.
19. The needle of claim 14, wherein:
said plurality of ports each have a cross-sectional area that is smaller than a cross-sectional area of said distal opening;
wherein said cross-sectional area of a port is measured in a plane perpendicular to a direction of fluid flow through said port; and
wherein said cross-sectional area of said distal opening is measured in a plane perpendicular to a direction of fluid flow through said distal opening.
20. The needle of claim 14, wherein:
said second lumen has a hydraulic diameter that is smaller than a hydraulic diameter of said first lumen.
21. The needle of claim 14, wherein said second elongated body has a sidewall defining said second lumen, said sidewall of said second elongated body having a thickness extending from an outward facing surface to an inward facing surface;
wherein said inward facing surface faces the second lumen; and
wherein said outward facing surface faces the sidewall of the first elongated body.

\* \* \* \* \*